US00PP35707P2

(12) United States Plant Patent
Ammerlaan

(10) Patent No.: US PP35,707 P2
(45) Date of Patent: Mar. 26, 2024

(54) ***GASTERALOE* PLANT NAMED 'OVROCKS11'**

(50) Latin Name: ***Aloe aristata* x *Gasteria carinata***
Varietal Denomination: OVROCKS11

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/445,502

(22) Filed: Sep. 5, 2023

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
CPC ..... A01H 6/00; A01H 5/12
See application file for complete search history.

*Primary Examiner* — Keith O. Robinson
(74) *Attorney, Agent, or Firm* — Samuel R. McCoy, Jr.

(57) ABSTRACT

A new and distinct x*Gasteraloe* plant named 'OVROCKS11' which is characterized by dark green carinate foliage that is moderately to densely covered with very light greyed-green protuberances, adaxial foliar protuberances are arranged in highly irregular transverse lines, abaxial foliar protuberances are arranged in distinct transverse lines, protuberances along the distal centerline of the abaxial foliar surface that are modified into spines and arranged in a distinct longitudinal line, and finely dentate margins with very light greyed-green teeth. The new variety has shown to be uniform and stable in the resulting generations from asexual propagation.

4 Drawing Sheets

Latin name of the genus and species: The Latin name of the genus and species of the novel variety disclosed herein is *Aloe aristata* x *Gasteria carinata*, which is synonymous with the nothogenus and species, x*Gasteraloe beguinii.*

Variety denomination: The inventive variety of x*Gasteraloe* disclosed herein has been given the variety denomination 'OVROCKS11'.

BACKGROUND OF THE INVENTION

Parentage: 'OVROCKS11' is a seedling selection resulting from the controlled pollination of an unnamed *Aloe variegata* plant (unpatented), the seed parent, with an unnamed *Gasteria carinata* plant (unpatented), the pollen parent. The crossing was made by the inventor in August of 2014 at a commercial greenhouse in Bleiswijk, the Netherlands. In early 2015, one seedling from said cross was observed to exhibit unique foliage and growth characteristics when compared to the parent plants and all other progenies. After confirming the stability of the unique characteristics first observed, the new plant was selected for commercialization and given the name, 'OVROCKS11'.

Asexual Reproduction: The variety now called 'OVROCKS11' was first asexually propagated by stem cuttings in March of 2015 at a greenhouse in Bleiswijk, The Netherlands and has since been vegetatively propagated through several additional generations. Through these subsequent generations, the unique features of this cultivar are stable and reproduced true to type.

SUMMARY OF THE INVENTION

The cultivar 'OVROCKS11' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS11'. These characteristics in combination distinguish 'OVROCKS11' as a new and distinct x*Gasteraloe* cultivar:

1. 'OVROCKS11' exhibits long, lanceolate foliage that is moderately concaved and carinate; and
2. 'OVROCKS11' exhibits relatively dark green foliage that is moderately to densely covered with very light greyed-green protuberances; and
3. 'OVROCKS11' exhibits adaxial foliar protuberances are arranged in highly irregular transverse lines across the laminar surface; and
4. 'OVROCKS11' exhibits abaxial foliar protuberances are arranged in distinct transverse lines across the laminar surface, with a small subset of protuberances along the distal centerline modified into spines and arranged in a distinct longitudinal line; and
5. 'OVROCKS11' exhibits finely dentate margins with very light greyed-green teeth, generally appearing as nearly white.

BOTANICAL DESCRIPTION OF THE PLANT

Figure 1:
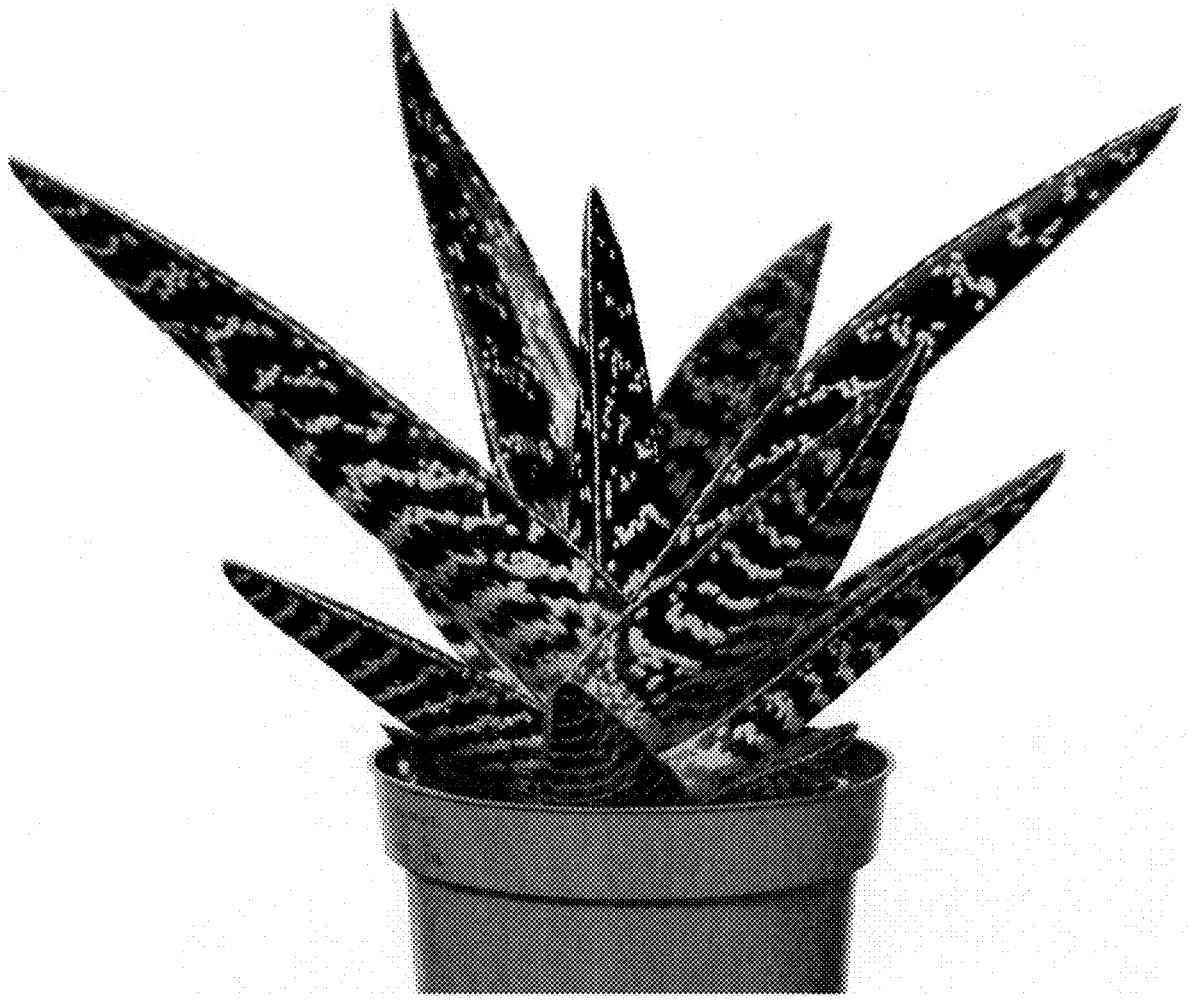
FIG. 1 illustrates, as nearly true as it is reasonably possible to make the same in color photographs of this type, an exemplary plant of 'OVROCKS11' grown in a commercial greenhouse in Bleiswijk, the Netherlands. This plant is approximately 2 years old, shown planted in a 12 cm container.
Figure 2:
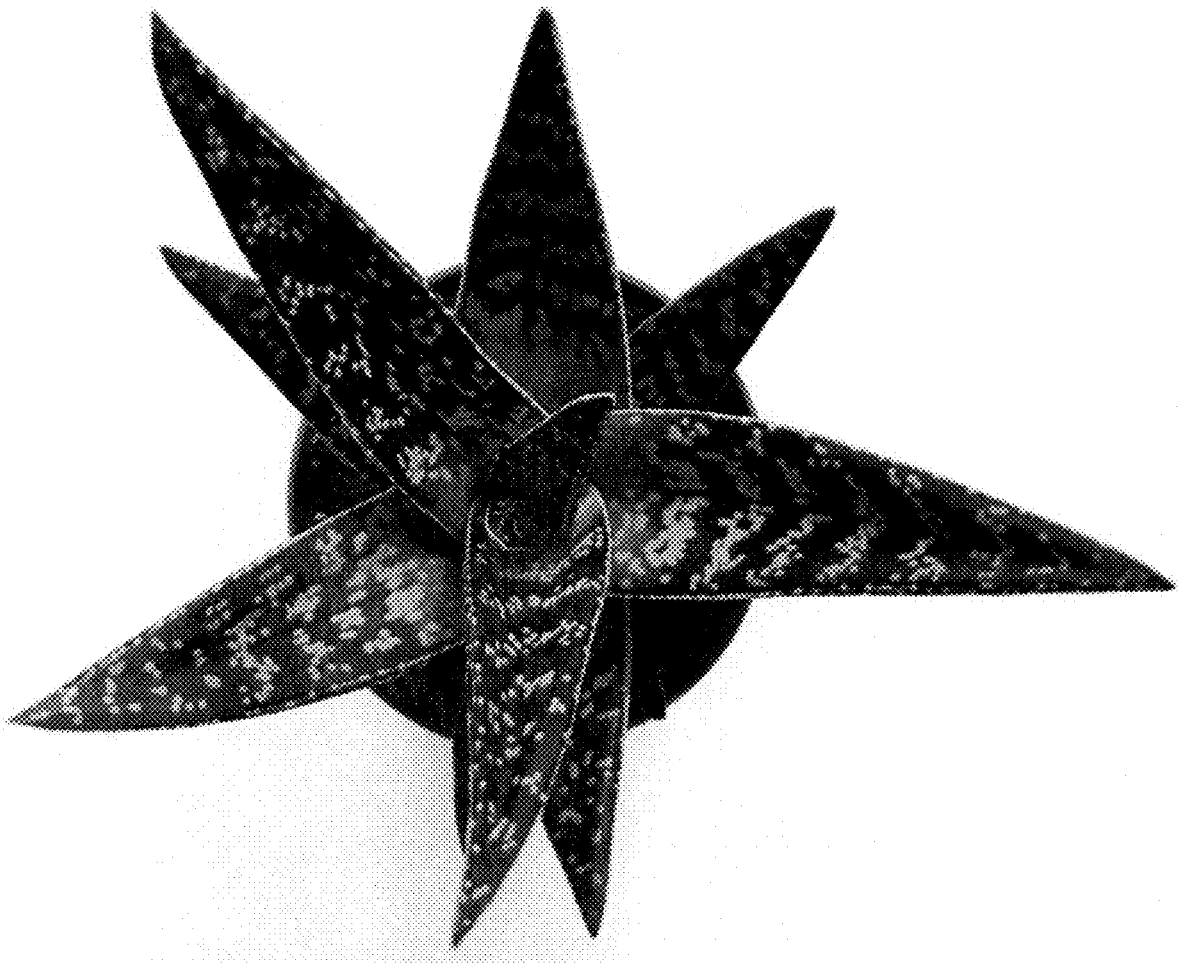
FIG. 2 illustrates, as nearly true as it is reasonably possible to make the same in color photographs of this type, the typical foliage arrangement of 'OVROCKS11'.
Figure 3:
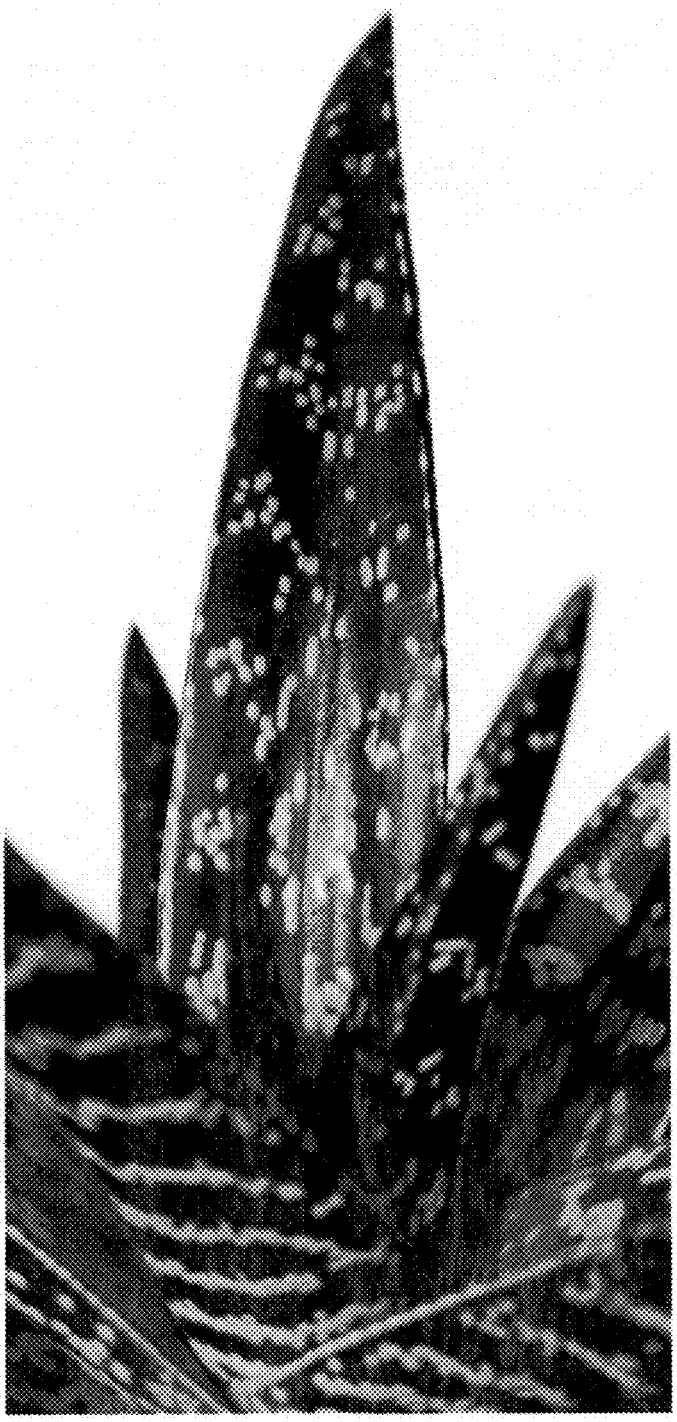
FIG. 3 illustrates, as nearly true as it is reasonably possible to make the same in color photographs of this type, the adaxial surface of the mature foliage 'OVROCKS11'.
Figure 4:
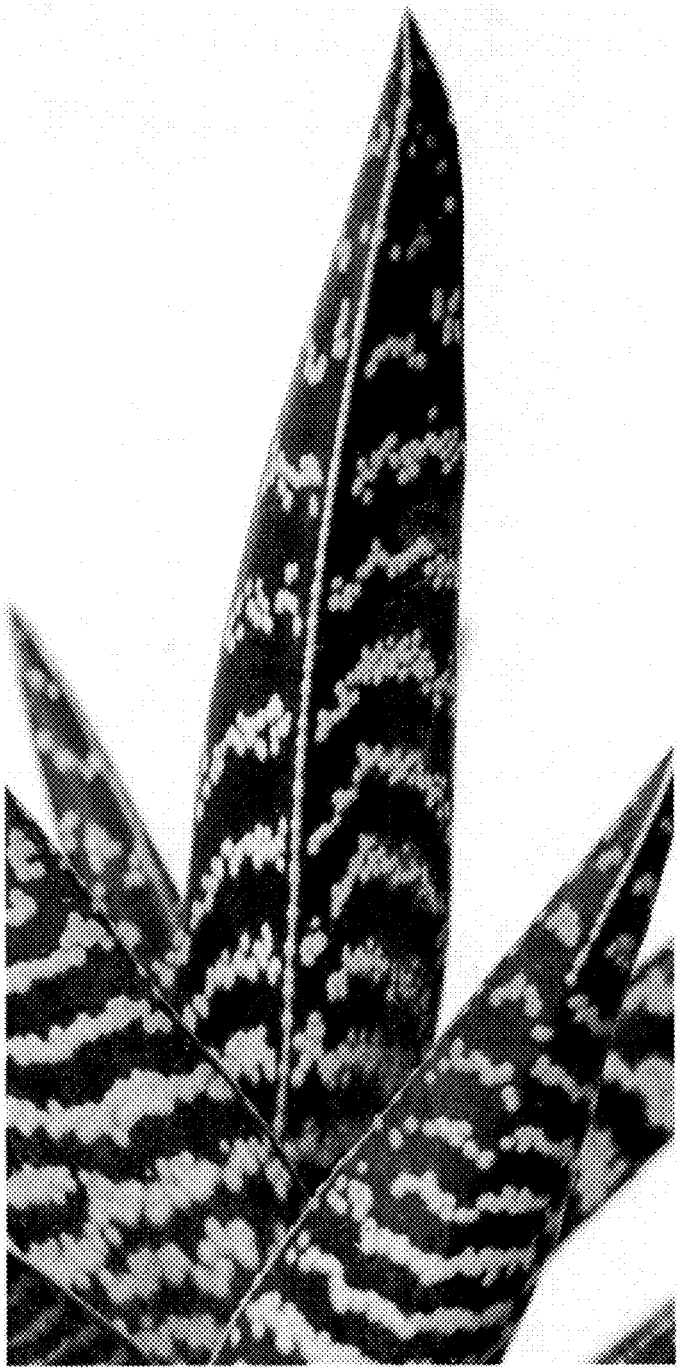
FIG. 4 illustrates, as nearly true as it is reasonably possible to make the same in color photographs of this type, the abaxial surface of the mature foliage 'OVROCKS11'.

The following observations and measurements made in February of 2023 describe averages from a sample set of six specimens of 2 years-old 'OVROCKS11' plants grown in 12 cm nursery containers at commercial greenhouse in Bleiswijk, the Netherlands. Plants were produced using conventional greenhouse production protocols for x*Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS11' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'OVROCKS11' and a comparison with the parents and closest known comparator is provided below.

Plant description:

*Growth habit.*—Succulent perennial with foliage growing in a compact basal rosette.

*Plant form.*—Broad obovate.

*Height from soil level to top of foliar plane.*—19.3 cm.

*Plant spread.*—Average of 23.5 cm.

*Plant Vigor.*—Moderately vigorous.

*Propagation.*—Type — Leaf cuttings. Time to initiate rooting — Approximately 5 weeks at an approximate temperature of 21 degrees Celsius. Crop time — Approximately 1 year to produce a marketable plant in a 9 cm container.

*Disease and pest resistance or susceptibility.*—Neither resistance nor susceptibility to typical x*Gasteraloe* pests and diseases has been observed.

*Environmental tolerances.*—Adapt to, at least, USDA Zones 10 to 12 and temperatures as high as 40 degrees Celsius; low tolerance to rain yet drought tolerant once established; high tolerance to wind.

Root system:

*General.*—Fine, well-branched fibrous roots.

Stems:

*Branching habit.*—No stems or branches; leaves arranged in a basal rosette.

Foliage:

*Arrangement.*—Spirally arranged in a basal rosette.

*Division.*—Simple.

*Attachment.*—Sessile.

*Quantity.*—Approximately 15 leaves per rosette.

*Shape.*—Lanceolate.

*Dimensions.*—17.7 cm long, 4.1 cm wide, and 1.5 cm thick.

*Aspect.*—Moderately concave, and carinate. In juvenile foliage, the distal portion of the lamina curls upward.

*Attitude.*—Foliage is held upright at and near the center of the rosettes and becomes progressively more relaxed towards the outer whorls of foliage, at an average angle of 30 degrees from horizontal.

*Apex.*—Narrowly acute.

*Base.*—Broad cuneate.

*Margin.*—Finely dentate; teeth have an average length of 0.5 cm and are colored greyed-green, nearest to in between RHS 192A and 192B. Margins are not undulated or lobed.

*Pubescence and texture.*—Juvenile foliage, adaxial surface — Glabrous, smooth, and sparsely covered with small, rounded to somewhat oblong protuberances that are arranged in highly irregularly transverse lines across the laminar surface; protuberances are approximately 0.2 cm long and 0.125 cm wide. Juvenile foliage, abaxial surface — Glabrous, smooth, and sparsely covered with small, rounded to somewhat oblong protuberances that are arranged in distinct transverse lines across the laminar surface; protuberances are approximately 0.2 cm long and 0.175 cm wide. Mature foliage, adaxial surface — Glabrous, smooth, and moderately covered with small, rounded to oblong protuberances that are arranged in highly irregularly transverse lines across the laminar surface; protuberances are approximately 0.25 cm long and 0.175 cm wide; protuberances reach a height of 0.2 mm towards the apex. Mature foliage, abaxial surface — Glabrous, smooth, and densely covered with small, round protuberances that are arranged in distinct transverse lines across the laminar surface; protuberances are approximately 0.2 cm in diameter. A small subset of protuberances along the distal centerline are arranged in a distinct line and are modified into spines that are approximately 0.06 cm in height.

*Luster of the adaxial surface.*—Moderately glossy.

*Luster of the abaxial surface.*—Slightly glossy.

*Color.*—Juvenile foliage, adaxial surface — Green to greyed-green, nearest to a mixture of RHS 139A and N189A, and transitioning to green towards the base, nearest to RHS 139A. Protuberances are colored greyed-green, distally, nearest to RHS 191A; protuberances become lighter, proximally, nearest to a mixture of RHS 191C. Juvenile foliage, abaxial surface — Nearest to a mixture of green and greyed-green, RHS 139A and N189A; transitioning to light green towards the base, nearest to RHS 137A. Protuberances are colored greyed-green, distally, nearest to RHS 192B; protuberances become lighter, proximally, nearest to a mixture of RHS 192D. Mature foliage, adaxial surface — Nearest to a mixture of green and greyed-green, RHS 139A and N189A yet nearest to N189A; transitioning to light yellow-green towards the base, nearest to a mixture of RHS 147A and 147B. Protuberances are colored greyed-green, distally, nearest to RHS 191A; protuberances become lighter, proximally, nearest to a mixture of RHS 191C. Mature foliage, abaxial surface — Greyed-green, nearest to RHS N189A; transitioning to light green towards the base, nearest to RHS 139A. Protuberances are colored greyed-green, distally, nearest to RHS 191B; protuberances become lighter, proximally, nearest to a mixture of RHS 191D, 192C, and 192D.

*Venation.*—Pattern — No venation is visible. Color, adaxial surface — No venation is visible. Color, abaxial surface — No venation is visible.

*Petiole.*—No petiole; leaves are sessile.

Inflorescence: No flowering has been observed to date.

Comparisons with the parent plants: Plants of the new cultivar 'OVROCKS11' differ from the seed parent, an unnamed *Aloe variegata* plant (not patented), in the following characteristics described in Table 1 below.

TABLE 1

| Characteristic | 'OVROCKS11' | The seed parent. |
|---|---|---|
| Growth habit. | Spirally arranged in a rossette. | Equitant to 3-ranked rosette. |
| Foliage shape. | Lanceolate. | Deltoid to broadly lanceolate. |
| General coloration of the foliage. | Darker green, relative to the parent. | Lighter green, relative to 'OVROCKS11', and narrowly margined white. |
| Foliar margins. | Finely dentate; teeth have an average length of 0.5 cm. | Finely crenate, with blunt teeth approximately 0.2 to 0.3 cm. |
| Prominence of foliar protuberances. | Less prominent. | More prominent. |

Plants of the new cultivar 'OVROCKS11' differ from the pollen parent, an unnamed *Gasteria carinata* plant (not patented), in the following characteristics described in Table 2 below.

TABLE 2

| Characteristic | 'OVROCKS11' | The pollen parent. |
|---|---|---|
| Growth habit. | Spirally arranged in a rossette. | Equitant to 3-ranked rosette. |
| Foliage aspect. | More carinate than the parent. | Less carinate than 'OVROCKS11'. |

TABLE 2-continued

| Characteristic | 'OVROCKS11' | The pollen parent. |
|---|---|---|
| Size of foliar protuberances. | Larger than the parent. | Smaller than 'OVROCKS11'. |
| Arrangement of foliar protuberances on the abaxial surface. | Arranged in distinct transverse lines across the lamina. | Varying from randomly distributed to loosely arranged in irregular transverse lines. |

Comparison with the closest known comparator: Plants of the new cultivar 'OVROCKS11' differ from the most similar variety known to the inventor, x*Gasteraloe* 'OVROCKS02' (U.S. Plant Pat. No. 30,136), in the following characteristics described in Table 3 below.

TABLE 3

| Characteristic | 'OVROCKS11' | 'OVROCKS02' |
|---|---|---|
| Growth habit. | Spirally arranged in a rosette; foliage is more loosely held in the rosette. | Spirally arranged in a rosette; foliage is more tightly held in the rosette. |
| Foliage abundance. | Less abundant. | More abundant. |
| Foliage shape. | Lanceolate. | Narrow deltoid. |
| General coloration of the foliage. | Dark green. | Dark green and margined with light green. |
| Foliar margins | Finely dentate, with small marginal teeth; more teeth than 'OVROCKS02'. | Dentate, with larger marginal teeth; fewer teeth than 'OVROCKS11'. |
| Size of foliar protuberances. | Smaller than the 'OVROCKS02'. | Larger than 'OVROCKS11'. |
| Arrangement of the foliar protuberances. | Arranged in distinct transverse lines across the lamina. | Varying from randomly distributed to loosely arranged in irregular transverse lines. |

That which is claimed is:

1. A new and distinct variety of x*Gasteraloe* plant named 'OVROCKS11', substantially as described and illustrated herein.

* * * * *